United States Patent
Prody (10) Patent No.: US 11,090,184 B1
(45) Date of Patent: Aug. 17, 2021

(54) SURGICAL DRAINAGE RESERVOIR SUPPORT

(71) Applicant: Mary Ann Robinson Prody, White Bear Lake, MN (US)

(72) Inventor: Mary Ann Robinson Prody, White Bear Lake, MN (US)

(*) Notice: Subject to any disclaimer, the term of this patent is extended or adjusted under 35 U.S.C. 154(b) by 0 days.

(21) Appl. No.: 17/173,893

(22) Filed: Feb. 11, 2021

Related U.S. Application Data (63) Continuation-in-part of application No. 16/419,703, filed on May 22, 2019, now abandoned, and a continuation of application No. 14/450,260, filed on Aug. 3, 2014, said application No. 16/419,703 is a continuation-in-part of application No. 14/450,260.

(60) Provisional application No. 61/958,662, filed on Aug. 3, 2013.

(51) Int. Cl.
*A61F 5/44* (2006.01)
*A61M 25/02* (2006.01)
*A61M 27/00* (2006.01)

(52) U.S. Cl.
CPC .......... *A61F 5/4408* (2013.01); *A61M 25/02* (2013.01); *A61M 27/00* (2013.01); *A61M 2025/0206* (2013.01); *A61M 2025/0213* (2013.01)

(58) Field of Classification Search
CPC ...... A61F 5/4408; A61M 25/02; A61M 27/00
USPC .......................................................... 604/327
See application file for complete search history.

(56) References Cited

U.S. PATENT DOCUMENTS

| | | | | |
|---|---|---|---|---|
| 4,067,337 A | * | 1/1978 | Ness | A61F 13/58 24/67 AR |
| 4,445,894 A | * | 5/1984 | Kovacs | A61M 25/02 128/DIG. 26 |
| 5,257,419 A | * | 11/1993 | Alexander | A61F 5/028 2/338 |
| 5,496,282 A | * | 3/1996 | Militzer | A61M 25/02 604/179 |
| 6,296,164 B1 | | 10/2001 | Russo | |
| 6,610,032 B1 | * | 8/2003 | Prody | A61M 27/00 604/179 |
| 6,678,898 B2 | * | 1/2004 | Jones | A41F 1/002 2/321 |
| 8,066,657 B2 | * | 11/2011 | Frazer | A61F 13/148 602/61 |
| 8,292,860 B1 | * | 10/2012 | Persichetti | A45F 3/14 604/355 |
| 2011/0034889 A1 | * | 2/2011 | Smith | A61F 5/449 604/327 |

* cited by examiner

*Primary Examiner* — Andrew J Mensh
(74) *Attorney, Agent, or Firm* — Berggren Law Offices LLC; William R Berggren (57) ABSTRACT

An improved surgical drainage reservoir support to securely support surgical drainage reservoirs with an easily located and grasped handles on the surface attachment elements containing multiple hooks.

9 Claims, 4 Drawing Sheets

SURGICAL DRAINAGE RESERVOIR SUPPORT

CROSS REFERENCE TO RELATED APPLICATIONS

The application listed below is a continuation in part of U.S. Ser. No. 16/419,703 filed May 22, 2019 that claims benefit of continuation in part of U.S. Ser. No. 14/450,260 filed on Aug. 3, 2014 that claims benefit of the earlier filing date under 35 USC 119(e) of provisional application No. 61/958,662 filed on Aug. 3, 2013.

FIELD OF THE INVENTION

This invention relates to surgical drainage reservoir supports and more particularly to an improved surgical drainage reservoir support to secure the drainage reservoirs within the sight and reach of the patient during recovery from surgery.

BACKGROUND OF THE INVENTION

Certain surgical procedures require surgical placement of a drainage tube into the body at the surgical site to remove drainage and promote surgical healing. The drainage tube is connected to a drainage reservoir that accumulates drainage, which is outside the body. The drainage reservoir is then emptied regularly, often several times a day, by clinicians and then patients are taught how to empty drainage reservoirs.

Supports for surgical drainage reservoirs whereby one or more drainage reservoir is easily and securely fastened to a band within sight and reach of the patient, such as the device described in U.S. Pat. No. 6,610,032 are very useful and prevent complications for post-surgical drainage from surgical sites requiring drainage devices. However, the fasteners of these supports are difficult to remove to release the reservoirs to be emptied and replaced by patients with arthritis or other disabilities, patients with diminished strength, such as from surgery, or clinicians, especially clinicians wearing surgical gloves.

What is needed is an improved surgical drainage device that allows humans with altered or limited dexterity such as patients with arthritis or other disabilities, patients with diminished strength, such as from surgery, or clinicians, especially clinicians wearing surgical gloves, to more easily access and use the described fasteners.

SUMMARY OF THE INVENTION

The surgical drainage reservoir support is a device to individually securely support one or more surgical drainage reservoirs and make them accessible to being emptied and reused more easily by clinicians wearing surgical gloves and patients with arthritis or weak from surgery. Specifically, the surgical drainage reservoir support, configured to be releasably attached to individual reservoirs by their apertures, comprises an elastic band, one or more elongated mechanical fasteners, and a handle on each. The elastic band has an outside surface, an inside surface opposite the outside surface, a first end and a second end adapted for extending around a body part of a patient, and comprises a mechanical fastener at a first end and near the second end configured for securing the band at a selected tightness about the body part of the patient, the elastic band being adjustable as to the selected tightness. The one or more spaced apart elongated mechanical fasteners attached to the outside surface of the band are the elongated mechanical fasteners aligned with a longitudinal axis of the elastic band. Each elongated mechanical fastener comprises a first surface attachment element having a first side with a multitude of loops and permanently affixed to the outside surface of the elastic band with the multitude of loops facing outward. Each also comprises a second surface attachment element having a first side with a multitude of hooks facing the first side with the multitude of loops, a second side that is textured to be configured for easy grasping, a first end permanently fastened to the first surface attachment element, a second end, and a length extending longitudinally in removable, mutually engaged contact with the first surface attachment element, the second surface attachment element configured to attach to the first surface attachment element sufficiently to hold a drainage reservoir when filled. The handle configured to permit easy removal of the second surface attachment element from the first surfaced attachment element to free the drainage reservoir and subsequent reattachment when the drainage reservoir is emptied and ready for reuse, and comprising an extension of the second surface attachment element from the second end of the second surface attachment element, the extension having its own end and first side with multiple hooks with the first side of the extension folded back upon itself so two surfaces having a multitude of hooks are in contact, the end of the extension is permanently affixed to the second surface attachment element to form a handle with an outside textured surface, a length at least 0.25 inches to be able to be easily gripped, and structure lifting off the plane of the elastic base below the handle at an angle of at least 10 degrees to provide easy gripping.

The method of using a surgical drainage reservoir support, configured to be releasably attached to individual drainage reservoirs by their support apertures, where the drainage reservoirs are attached to a patient, comprising seven steps. One step is providing one or more drainage reservoirs attached to the patient for collecting the fluid, each drainage reservoir having an aperture associated therewith for releasably affixing the one or more drainage reservoirs individually to the surgical drainage reservoir support. Another step is providing a surgical drainage reservoir support for supporting one or more drainage reservoirs attached to a patient, each drainage reservoir configured to be releasably attached to the device by its aperture, the surgical drainage reservoir support comprising the elements of an elastic band, one or more elongated mechanical fasteners, and a handle on each as discussed above. Still another step is placing the elastic band around a body part of the patient at a selected tightness affixing the apparatus to the patient with the drainage reservoirs affixed to drainage lines extending from the patient. Another step is gripping the handle of the one or more fasteners and easily opening each fastener, attaching one drainage reservoir to each fastener, and closing each fastener to attach the drainage reservoir to the apparatus and to the patient. Another step is repeating as necessary until all drainage reservoirs are attached to the apparatus and the patient. Still another step is periodically gripping the handle of one or more fasteners and easily opening the fastener to remove the drainage reservoir from the device to empty it. Another step is reattaching the drainage reservoir to the device to continue collecting fluid.

The method of using a surgical drainage reservoir support system for collecting a bodily fluid in a medical draining procedure, comprising: six steps. One step is providing a surgical drainage reservoir support system for collecting a bodily fluid in a medical draining procedure, the surgical drainage reservoir support system comprising the elements of an elastic band, one or more elongated mechanical fasteners, and a handle on each as discussed above and at least one drainage reservoir. Each drainage reservoir has an attachment band comprising a loop adapted for receiving one end of said second surface attachment element for engaging the drainage reservoir with the attaching band for displacing the drainage reservoir within reach of a patient wearing the attaching band. Another step is placing the elastic band around a body part of the patient at a selected tightness to releasably affix the drainage reservoir support to the patient with the drainage reservoirs affixed to drainage lines extending from the patient. Still another step is gripping the handle of the one or more elongated mechanical fasteners and easily opening each elongated mechanical fastener, attaching one drainage reservoir to each elongated mechanical fastener, and closing each elongated mechanical fastener to releasably attach the drainage reservoir to the surgical drainage reservoir support and to the patient. Another step is repeating as necessary until all drainage reservoirs are attached to the surgical drainage reservoir support and the patient. Another step is periodically gripping the handle of one or more fasteners and easily open the fastener to remove the drainage reservoir from the surgical drainage reservoir support to empty it. Still another step is reattaching the drainage reservoir to the surgical drainage reservoir support to continue collecting fluid.

The surgical drainage reservoir support article and method aspects of the invention provide an improvement over devices that are known. The invention improves the ease that a patient and clinician can use this device by providing a handle, or gripping surface, to the end of the elongated second surface attachment element of the elongated mechanical fastener that hold each drainage reservoir securely in place until removed, emptied and reattached. The handle allows patients with arthritis, patents having post operation weakness or clinicians wearing surgical gloves, to more easily opening of the fastener, which by description of a hook and loop closure is so secure it can present a challenge when removing and reattached.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF SOME EMBODIMENTS OF THE INVENTION

This invention is an improved securement of surgical drainage reservoirs while improving the ease with which clinicians and patients can use this device. This improvement provides a handle, or gripping surface, to the end of the second surface attachment element. The handle allows the clinician or the patient easier opening of the elongated mechanical fastener, that is so secure it can present a challenge when removing drainage reservoirs for emptying and replacing them for further fluid collection during the early post-surgery healing process. This improvement is particularly useful for three classes of people. Patients with arthritis, post-surgical patients with generalized muscle weakness, and clinicians or patients wearing gloves such as, for example, medical or surgical gloves.

Some patients who are dealing with collection of fluid over time have arthritis that results in diminished or altered dexterity. Arthritis causes hand and finger weakness due to inflammation and loss of cartilage which functionally changes a grip. Moreover, arthritis in fingers and thumbs is very common. Arthritis of the thumb causes gripping and pinching to be very painful and can result in significant disability. 100% of gripping requires a functioning thumb. Decreased or altered dexterity in fingers would be due to any musculoskeletal, neuromuscular conditions or a multitude of disease processes which would affect hand/finger dexterity-decreased strength and function.

For this class, some embodiments of invention provide two main benefits. Firstly, the handle structure of a double looped hook surfacer attachment element, folded over itself and sewn or permanently attached to itself, with a short length on the order of about 0.25 to over 0.50 inch from the end of the second service attachment surface, and with a slightly raised angle from the plane of the band below the handle provides the handle visible and tactile distinction between the gripping end of the second surface attachment element releasably attached to the first surface attachment element and end that is permanently attached flat end. Secondly, this construction also provides a handle that is stiff enough to grip for an easier lifting of the second surface attachment element that without handle typically has a length of about 2 to over 3 inches of mechanical fastener. This mechanical fastener length of flat engaged hook and loop surface attachment length of about 2 to over 3 inches creates a closure that is so secure it can present a challenge for this class to separate without a handle when removing and replacing drainage reservoirs for emptying of drainage fluid that typically needs to be done several times per day.

Some patients who are dealing with collection of fluid over time are post-surgical patients with generalized muscle weakness, fatigue, and decreased concentration. There is generally universal post-surgery fatigue and weakness due to the surgical trauma and healing process, anesthesia, pain, medications as well as decreased concentration. Fatigue and generalized weakness compromises muscular strength including grip strength. Performing a medical procedure, in this case emptying drainage from a drainage reservoir connected to a drainage tube inserted into the body often causes anxiety and requires mental concentration to do the procedure often and correctly.

For this class, some embodiments of invention provide three main benefits. Firstly, as for the previous class, the handle structure of a double looped hook surfacer attachment element, folded over itself and sewn or permanently attached to itself, with a short length, generally on the order of about 0.25 to over 0.50 inch from the end of the second service attachment surface, and with a slightly raised angle from the plane of the band below the handle provides the handle visible and tactile distinction between the gripping end of the second surface attachment element releasably attached to the first surface attachment element and end that is permanently attached flat end. Secondly, as for the previous class, this construction also provides a handle that is stiff enough to grip for an easier lifting of the second surface attachment element that without handle typically has a length of about 2 to over 3 inches of mechanical fastener. This mechanical fastener length of flat engaged hook and loop surface attachment length of about 2 to over 3 inches creates a closure that is so secure it can present a challenge for this class to separate without a handle when removing and replacing drainage reservoirs for emptying of drainage fluid that typically needs to be done several times per day. Thirdly, the slightly raised angle of the handle, remains slightly raised so when the drainage reservoir is removed and the hook and loop usually re-engages during movement, the easily visible handle is ready to grip for an easier lifting of the flat portion of the second surface attachment element from the loop surface of the first surface attachment element to engaged the second surface attachment element with the drainage reservoir to re-attach the drainage reservoir with the surgical drainage reservoir support.

Some people who are dealing with collection of fluid over time are clinicians or patients or caregivers wearing medical or surgical gloves. When wearing medical or surgical gloves manual dexterity can be compromised due to reduced sensation, decreased touch sensitivity and tactility. Frictional properties such as gripping and non-slippage are less than optimal when wearing gloves. Adherence to objects is decreased when using a dexterity function such as gripping. Objects are more likely to slip when performing procedures such as removing a second surface attachment element from a first surface attachment element when removing a drainage reservoir for fluid removal or replacing it for further fluid gathering.

For this class, some embodiments of invention provide a main benefit. The backing of the extended portion of the handle, as well as the entire second surface attachment element, is textured. When the surfaced is folded over itself and sewn or otherwise permanently fastened together with a length of between 0.25 and 0.5 inch with a slightly raised angle from the plain of the first surface attachment element a handle is made with textured outer surfaces. The two textured surfaces allow better gripping with more traction and friction between the handle and a gloved index finger and thumb. Gripping is done with adherence between the glove surfaces and the handle surfaces to grip with better adherence that provides improved dexterity and with enough stiffness to grip for an easier lifting of the flat engaged second surface attachment element of the mechanical fastener from the first surface attachment element.

Specifically, the article of the invention, the surgical drainage reservoir support, is configured to be releasably attached to individual reservoirs by their apertures, comprises an elastic band, one or more elongated mechanical fasteners, and a handle on each. The elastic band has an outside surface, an inside surface opposite the outside surface, a first end and a second end adapted for extending around a body part of a patient, and comprises a mechanical fastener at a first end and near the second end configured for securing the band at a selected tightness about the body part of the patient, the elastic band being adjustable as to the selected tightness.

In a first embodiment, the elastic band is an elastic band made of such material as, for example, elastic polyester and having one first surface attachment element comprising multiple loops facing upward and affixed to the top surface near the second end with the loops facing outward, and a second surface attachment element having a front side with multiple hooks facing downward, a backside with half permanently adhered to the underside of the first end of the band and the second half extending outward from the first end of the band. The front side of the second surface attachment element is configured to releasably affix to the multiple loops at the second end of the band to achieve a desired tightness around a patient.

In a second embodiment, the elastic band is an elastic band having at least two layers, one underlayer made of such elastic material as, for example, elastic polyester and having and a second side, and one top layer made of multiple loop fabric such as, for example, cotton having a first side configured with a multitude of loops and a second side where the second side is affixed to the first side of the elastic material. The first side of the cotton is the same as the first surface attachment element of the mechanical fastener facing outward. A second surface attachment element having a front side with multiple hooks facing downward, a backside with a first half permanently adhered to the underside of the first end of the band and a second half extending outward from the first end of the band. The front side of the second surface attachment element is configured to releasably to the multiple loops of the top layer of the band near the second end to achieve a desired tightness around a patient.

The one or more spaced apart elongated mechanical fasteners attached to the outside surface of the band are the elongated mechanical fasteners aligned with a longitudinal axis of the elastic band. Each elongated mechanical fastener comprises a first surface attachment element having a first side with a multitude of loops and permanently affixed to the outside surface of the elastic band with the multitude of loops facing outward. Each also comprises a second surface attachment element having a first side with a multitude of hooks facing the first side with the multitude of loops, a second side that is textured to be configured for easy grasping, a first end permanently fastened to the first surface attachment element, a second end, and a length extending longitudinally in removable, mutually engaged contact with the first surface attachment element, the second surface attachment element configured to attach to the first surface attachment element sufficiently to hold a drainage reservoir when filled.

Each length and width constructed to pass through the loop attached to the top of the drainage bulb and attach on both sides of the loop to the elongated first surface attachment element with enough area to provide attachment force that is sufficient to hold the drainage bulb when it is full without prematurely disconnecting and letting the drainage bulb fall and yank the drainage tube loose from the surgical site. It has been found that a length of between two inches and three inches and a width of about one inch provides suitable holding power and permits several longitudinal second surface attachment elements to be placed along regions of the elastic band. In some embodiments, both elements have a length of about 2 to over 3 inches. This allows second attachment elements to be placed on a support band with four elements holding four drainage reservoirs being comfortably in the front half of the support to permit easy patient access during emptying.

In the first embodiment mentioned above, one or more first surface attachment elements are affixed about the top surface of the elastic band on both sides of the first end of the elastic band and second end of the elastic band with the loops facing outward. One or more second surface attachment elements with hooks facing downward are placed above each elongated first attachment element.

In the second embodiment mentioned above, the entire top surface of the elastic band is a first surface attachment element and one or more second surface attachment elements with hooks facing downward are placed on both sides of the first end of the elastic band and second end of the elastic band.

The handle is configured to permit easy removal of the second surface attachment element from the first surfaced attachment element to free the drainage reservoir and subsequent reattachment when the drainage reservoir is emptied and ready for reuse. It comprises an extension of the second surface attachment element from the second end of the second surface attachment element. The extension has its own end and first side with multiple hooks with the first side of the extension folded back upon itself so two surfaces having a multitude of hooks are in contact, the end of the extension is permanently affixed to the second surface attachment element to form a handle with an outside textured surface, a length at least 0.25 inches to be able to be easily gripped, and structure lifting off the plane of the elastic band below the handle at an angle of at least 10 degrees to provide easy gripping. Affixing may occur by any means including, for example, sewing or stapling, preferably with non-metallic staples. In some embodiments, the angle is up to 20 degrees, up to 30 degrees up to 40 degrees, or up to 50 degrees or more. After several uses, the angle between the handle and the plane of the elastic band below the handle tends to increase resulting in even easier physical and tactile locating of the handle by patients and other users.

The surgical drainage reservoir support is designed to support surgical drains such as those commonly known as the Jackson-Pratt drains. These are two-piece suction drains that include a drainage tube connected to a drainage reservoir. The drainage tube is inserted into a surgical site to collect fluid and exited form the body and connected to the suction reservoir or bulb to collect drainage. Drainage reservoirs are sometimes flexible to permit squeezing of the drainage reservoir during drainage and sometimes transparent to permit visual notice of how full the drainage reservoir is at a given time. They generally have nipples to connect the drainage tube and stoppered drain openings to permit periodic emptying of the drainage reservoirs, as necessary. The drainage reservoirs also have a loop of material attached at the top from which to suspend the drainage reservoirs during drainage. Drainage reservoirs known as Jackson-Pratt drains are currently manufactured by many as the patents have expired. Some manufacturers include, for example, Cardinal Health of Dublin, Ohio, McKesson Corporation of Irving, Tex., and C.R. Bard Inc. of Murray Hill, N.J.

Each loop fits around a second surface attachment element that is then releasably attached to the first surface attachment element to securely store the drainage bulb during drainage. The second surface attachment element has a length and width constructed to pass through the loop attached to the top of the drainage reservoir and attach on both sides of the loop to the first surface attachment element with enough area to provide attachment force that is sufficient to hold the drainage reservoir when it is full without prematurely disconnecting and letting the drainage bulb fall and yank the drainage tube loose from the surgical site. It has been found that a length of about 2 to over 3 inches and a width of about one inch provides suitable holding power and permits several second surface attachment elements to be places along the length of the elastic band. The length and width of the second surface attachment element depends on the mechanical fastener components that are chosen, whether they create stronger or weaker attachment forces. Stronger attachment forces would require less area of attraction between the loop and hook surfaces to balance the ease of a person to free the drainage reservoirs for emptying with the elimination of risk of premature detachment of the fasteners that would cause undesirable freeing of the drainage reservoirs. Weaker attachment would require more area to balance the ease of a person to free the drainage reservoirs for drainage and the elimination of risk of premature detachment of the fasteners that would cause undesirable freeing of the drainage reservoirs.

Figure 1:
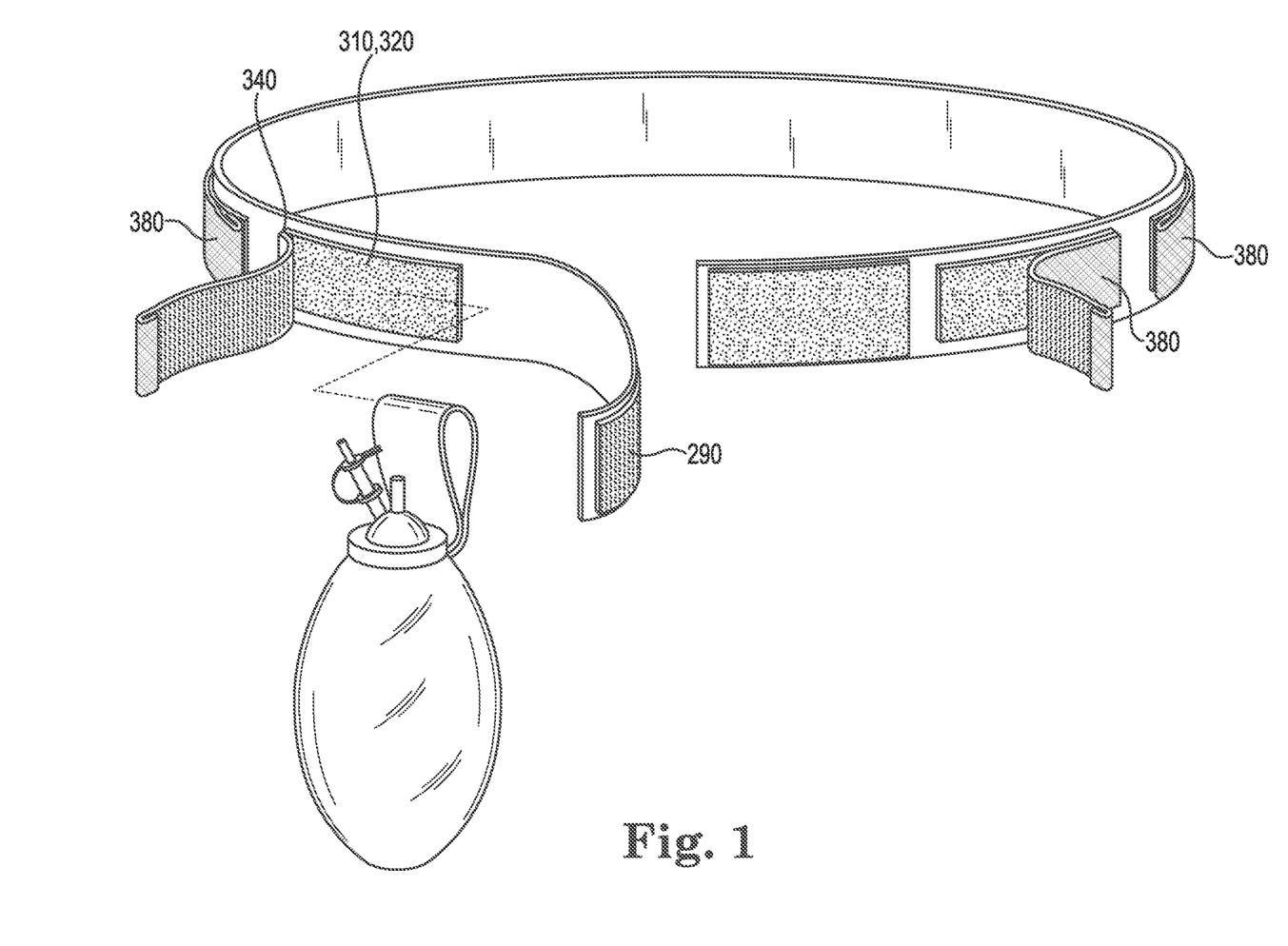
FIG. 1 is a perspective view of an embodiment of the invention.

Figures of several embodiments further illustrate aspects of the invention. FIG. 1 is a perspective view of an embodiment of the invention. Shown is a surgical drainage reservoir support (100) with an elastic band (200) that has an outside surface (220), an inside surface (230), a first end (240), a second region (250), an elastic material (260), and a means to secure the elastic band to itself comprising a first surface attachment element with a multitude of loops on one side and second surface attachment element with a multitude of hooks on one side. Also seen is one surgical drainage reservoir (A) with a loop (B), a stoppered drainage reservoir opening (C), and a nipple (D) to attach a drainage tube from a surgical site (not shown). At least one elongated mechanical fastener (300) is shown partially detached with a first surface attachment element (310) with a first side (320) with loops, a second side (330) permanently affixed to the outside surface of elastic band 200, a first end (340), and a second end (350) permanently affixed to outside surface 220 of elastic band 200. The at least one elongated mechanical fastener 300 is also shown with a second surface attachment element (360) with a first side (370), a second side (380) that is textured, a first end (390), and a second end (395). At least one handle (400) is shown with an extension element end (410), a handle outside (420) with a textured surface, a handle inside (440) with a multitude of hooks, a handle bonding region (440) (in this case by sewing thread), and a handle end (450).

Figure 2:
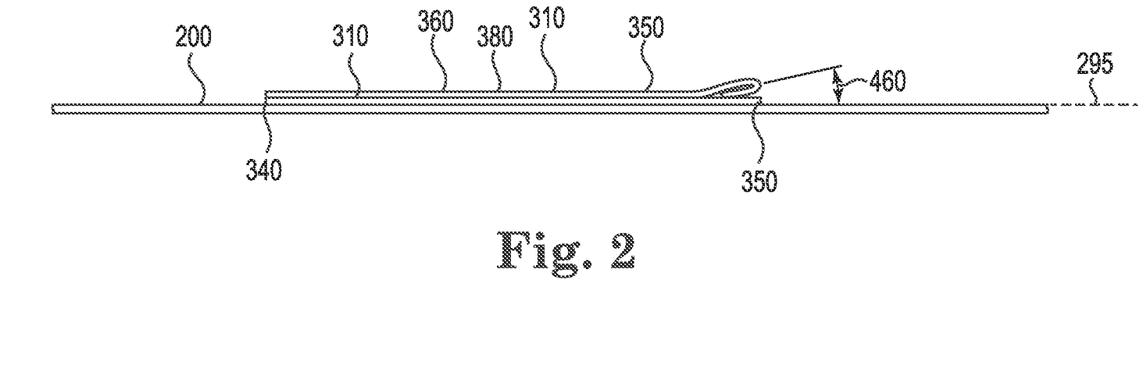
FIG. 2 is a top view of the embodiment shown in FIG. 1.

FIG. 2 is a top view of the embodiment shown in FIG. 1. Shown is elastic band 200, first surface attachment element 310, second surface attachment element 360, and handle 400 with an angle of elevation (460) above the plane of the base that is directly below it.

Figure 3:
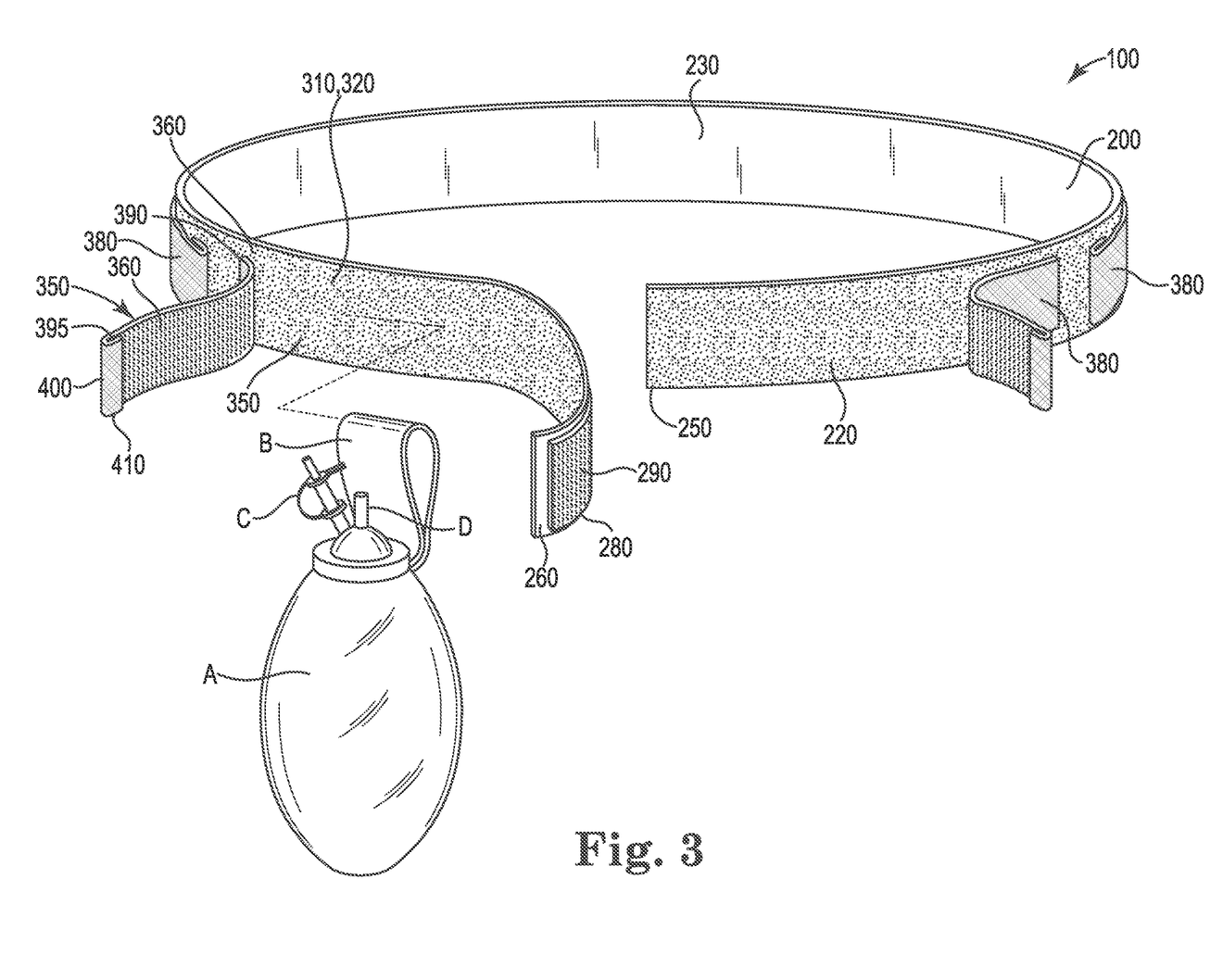
FIG. 3 is a perspective view of a second embodiment of the invention.

FIG. 3 is a perspective view of a second embodiment of the invention. Shown are surgical drainage reservoir support 100 with elastic band 200 that has an outside surface 220, inside surface 230, first end 240, second region 250, elastic material 260, loop fabric 270, and a means to secure the band to itself comprising a first surface attachment element with a multitude of loops on one side and second surface attachment element with a multitude of hooks on one side. Also seen is one surgical drainage reservoir A with loop B, stoppered drainage reservoir opening C, and nipple D to attach a drainage tube from a surgical site (not shown). At least one elongated mechanical fastener 300 is shown with a first surface attachment element 310 affixed to the entire outside surface 220 of elastic band 200 with first side 320 with loops, second side 330 permanently affixed to the outside surface of the elastic band 200, first end 340, and second end 350 permanently affixed to outside surface 220 of elastic band 200. At least one elongated mechanical fastener 300 is also shown with second surface attachment element 360 with first side 370, second side 380 that is textured, first end 390, and second end 395. At least one handle 400 is shown with extension element end 410, handle outside 420 with a textured surface, handle inside 440 with a multitude of hooks, handle bonding region 440 (in this case by sewing thread), and handle end 450.

Figure 4:
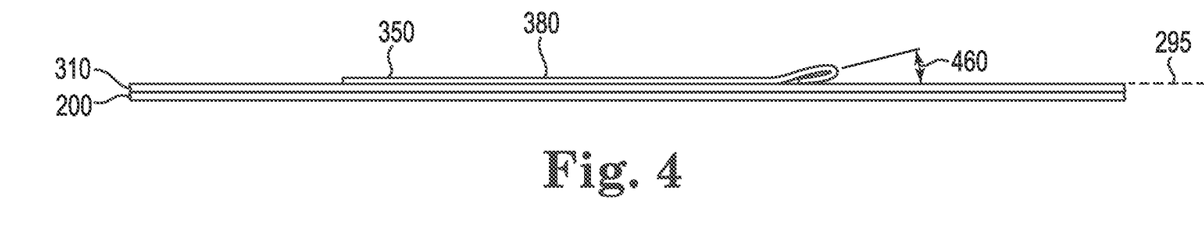
FIG. 4 is a top view of the embodiment shown in FIG. 3.

FIG. 4 is a top view of the embodiment shown in FIG. 3. Shown is elastic band 200, first surface attachment element 310 covering the entire outside surface 210 of elastic band 200, second surface attachment element 360, and handle 400 with angle of elevation 460 above the plane of the base that is directly below it.

Figure 5:
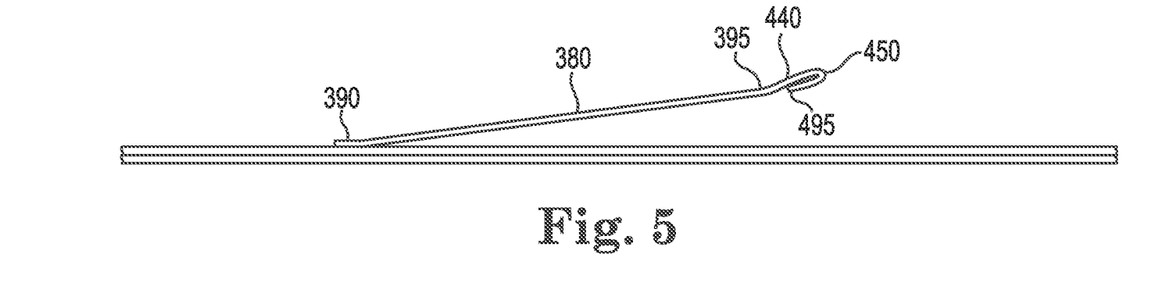
FIG. 5 is a top view of the embodiment of FIG. 3 with a second surface attachment element peeled away from a first surface attachment element.

FIG. 5 is a top view of the embodiment of FIG. 3 with a second surface attachment element peeled away from a first surface attachment element. Shown are elastic band 200 and elongated mechanical fastener 300 with first surface attachment element 310 covering the entire outside surface 210 of elastic band 200, second surface attachment element 360, and handle 400. Second surface attachment element 360 is shown with first side 370 with hooks at its first end 390 permanently fastened to first surface attachment 310, with the balance of second surface attachment element 360 detached from elongated first surface attachment element 310 to permit loop B to be slide over second attachment surface element 360 before it is reattached to first surface attachment element 310.

Figure 6:
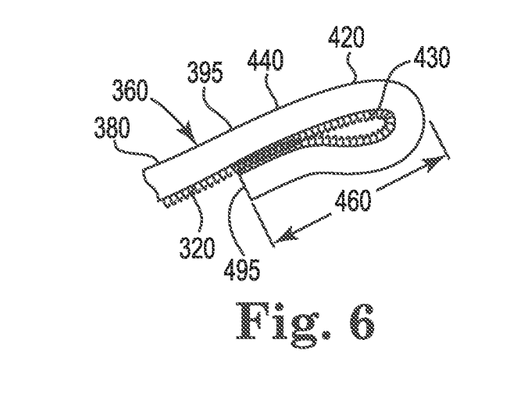
FIG. 6 is a closeup of the top view of a handle from FIG. 3.

FIG. 6 is a closeup of the top view of a handle from FIG. 3. Handle 400 is shown extending from second end 395 of second surface attachment element 360. The extension is looped with handle outside 320 being textured and the handle inside 430 having a multitude of hooks and facing and contacting each other. Shown near extension end 410, the two parts of the handle are fastened together permanently by sewing to form handle 400.

The method of using the invention has two aspects, (1) the method of using a surgical drainage reservoir support, configured to be releasably attached to individual drainage reservoirs by their support apertures, where the drainage reservoirs are attached to a patient and (2) the method of using a surgical drainage reservoir support system for collecting a bodily fluid in a medical draining procedure.

The first comprises seven steps. One step is providing one or more drainage reservoirs attached to the patient for collecting the fluid, each drainage reservoir having an aperture associated therewith for releasably affixing the one or more drainage reservoirs individually to the surgical drainage reservoir support.

Another step is providing a surgical drainage reservoir support for supporting one or more drainage reservoirs attached to a patient, each drainage reservoir configured to be releasably attached to the device by its aperture, the surgical drainage reservoir support comprising the elements of an elastic band, one or more elongated mechanical fasteners, and a handle on each as discussed above.

Still another step is placing the elastic band around a body part of the patient at a selected tightness affixing the apparatus to the patient with the drainage reservoirs affixed to drainage lines extending from the patient.

Another step is gripping the handle of the one or more fasteners and easily opening each fastener, attaching one drainage reservoir to each fastener, and closing each fastener to attach the drainage reservoir to the apparatus and to the patient.

Another step is repeating as necessary until all drainage reservoirs are attached to the apparatus and the patient.

Still another step is periodically gripping the handle of one or more fasteners and easily opening the fastener to remove the drainage reservoir from the device to empty it.

Another step is reattaching the drainage reservoir to the device to continue collecting fluid.

The second method aspect comprises six steps. One step is providing a surgical drainage reservoir support for collecting a bodily fluid in a medical draining procedure as described above. The surgical drainage reservoir support system comprising the elements of an elastic band, one or more elongated mechanical fasteners, and a handle on each as discussed above and at least one drainage reservoir. Each drainage reservoir has an attachment band comprising a loop adapted for receiving one end of said second surface attachment element for engaging the drainage reservoir with the attaching band for displacing the drainage reservoir within reach of a patient wearing the attaching band.

Another step is placing the elastic band around a body part of the patient at a selected tightness to releasably affix the drainage reservoir support to the patient with the drainage reservoirs affixed to drainage lines extending from the patient.

Still another step is gripping the handle of the one or more elongated mechanical fasteners and easily opening each elongated mechanical fastener, attaching one drainage reservoir to each elongated mechanical fastener, and closing each elongated mechanical fastener to releasably attach the drainage reservoir to the surgical drainage reservoir support and to the patient.

Another step is repeating as necessary until all drainage reservoirs are attached to the surgical drainage reservoir support and the patient.

Another step is periodically gripping the handle of one or more fasteners and easily open the fastener to remove the drainage reservoir from the surgical drainage reservoir support to empty it.

Still another step is reattaching the drainage reservoir to the surgical drainage reservoir support to continue collecting fluid.

In operation, a vertebrate patient would apply, or have applied for them, the elastic band around a vertebrate body part and secured at a selected tightness, the fastening means being adjustable as to said tightness. The patient may adjust the size for a comfortable and secure fit, or have it so adjusted for them. In function, the elastic band will securely support surgical drainage reservoirs extending from a patient's body. Surgical tube extending from a patient's body with an attached drainage reservoir would be securely supported by gripping force of elongated mechanical fastener. The second surface attachment element with a multitude of hooks on the inside surface is then manually pulled away from its companion first surface attachment with a multitude of loops on its outer surface by easily locating the handle affixed to the end of the second attachment element that is slightly raised above the plane of the base below it, stiff, thicker than the second surface attachment element and covered with a textured surface. The second surface attachment element is detached from the first attachment surface and is threaded through the loop on the surgical drainage device and securely supported by reattaching the second surface attachment element to the first surface attachment element. The process is repeated when the drainage reservoir is full and needs to be emptied and replaced upon the band to receive more fluid.

A patient may have one or more surgical drainage reservoirs at one time extending from the patient's body, which would allow the patient to utilize a surgical drainage reservoir support with one of more mechanical fasteners on either side of the elastic band connection region and corresponding with the location of the surgical drainage devices extending from the patient's body.

I claim:

1. A method of using a surgical drainage reservoir support, configured to be releasably attached to individual drainage reservoirs by their support apertures, where the drainage reservoirs are configured to be attached to a patient, comprising:

provinding one or more drainage reservoirs attached to the patient for collecting fluid, each drainage reservoir having an aperture associated therewith for releasably affixing the one or more drainage reservoirs individually to the surgical drainage reservoir support;

providing the surgical drainage reservoir support for supporting the one or more drainage reservoirs attached to the patient, each drainage reservoir configured to be releasably attached to the surgical drainage reservoir support by its aperture, the surgical drainage reservoir support comprising:

an elastic band, having an outside surface and an inside surface opposite the outside surface, a first end and a second end adapted for extending around a body part of a patient, and comprises a mechanical fastener at the first end and near the second end configured for securing the elastic band at a selected tightness about the body part of the patient, the elastic band being adjustable as to the selected tightness;

one or more spaced apart elongated mechanic al fasteners attached to the outside surface of the elastic band, the elongated mechanical fasteners aligned with a longitudinal axis of the elastic band, each elongated mechanical fastener comprises a first surface attachment element having a first side with a multitude of loops and permanently affixed to the outside surface of the elastic band with the multitude of loops facing outward, and a second surface attachment element having a first side with a multitude of hooks facing the first side with the multitude of loops, a second side that is textured to be configured for easy grasping, a first end permanently fastened to the first surface attachment element, a second end, and a length extending longitudinally in removable, mutually engaged contact with the first surface attachment element, the second surface attachment element configured to attach to the first surface attachment element sufficiently to hold the drainage reservoir when filled; and a handle configured to permit easy removal of the second surface attachment element from the first surfaced attachment element to free the drainage reservoir and subsequent reattachment when the drainage reservoir is emptied and ready for reuse, and the handle comprising an extension of the second surface attachment element from the second end of the second surface attachment element, the extension having its own end and first side with multiple hooks with the first side of the extension folded back upon itself so two surfaces having a multitude of hooks are in contact, the end of the extension is permanently affixed to the second surface attachment element to form the handle which includes an outside textured surface, a length of between 0.25 inches and 0.75 inches and structure that lifts off of and extends outward from the elastic band at an angle of between 10 degrees and 40 degrees from the plane of the elastic band below the handle, for providing a visible and tactile distinction between the handle and the permanently attached first end of the second surface attachment element, as well as providing easier grasping to and gripping of the handle, so that the handle is configured to be gripped by a clinician wearing surgical gloves with limited dexterity or gripped by a patient having diminished dexterity or strength;

placing the elastic hand around the body part of the patient at the selected tightness, affixing the surgical drainage reservoir support to the patient with the drainage reservoirs affixed to drainage lines extending from the patient;

gripping the handle of the one or more fasteners and easily opening each fastener, attaching one drainage reservoir to each fastener, and closing each fastener to attach the drainage reservoir to the surgical drainage reservoir support and to the patient;

repeating as necessary until all drainage reservoirs are attached to the surgical drainage reservoir support and the patient;

periodically gripping the handle of one or more fasteners and easily opening the fastener to remove the drainage reservoir from the surgical drainage reservoir support to empty it; and reattaching the drainage reservoir to the surgical drainage reservoir support to continue collecting fluid.

2. The method of claim 1, wherein each mechanical fastener is substantially aligned with the longitudinal axis of the elastic band.

3. The method of claim 1 wherein the elastic band includes a plurality of second surface attachment elements respectively associated with each mechanical fastener, each second surface attachment element being permanently affixed with the elastic band to releasably engage the second end of the fastener associated therewith.

4. The method of claim 1, wherein the drainage reservoir comprises: an attachment band comprising a loop adapted for receiving one end of said second surface attachment element for engaging the drainage reservoir with the elastic band for disposing the drainage reservoir within reach of the patient wearing the elastic band.

5. The method of claim 1, wherein the drainage reservoir comprises a flexible reservoir enabled for expulsion of the fluid stored therein by compressing the drainage reservoir.

6. The method of claim 1, wherein the drainage reservoir comprises a transparent material to enable an individual, who is the clinician or the patient, to see when the drainage reservoir is filled.

7. The method of claim 3, wherein the plural spaced apart elongate fasteners comprise at least one such fastener on each side of the elastic band, and the elongated fasteners are placed frontally to be within normal visual access of the individual.

8. The method of claim 1, wherein the first end of at least one of the one or more fasteners is sewn to the elastic band.

9. A method of using a surgical drainage reservoir support system for collecting bodily fluid in a medical draining procedure, the method comprising, providing a surgical drainage reservoir support for collecting a bodily fluid in the medical draining procedure, the surgical drainage reservoir support system comprising:
- an elastic band, having an outside surface and an inside surface opposite the outside surface, a first end and a second end adapted for extending around a body part of a patient, and comprises a mechanical fastener at a first end and near the second end configured for securing the band at a selected tightness about the body part of the patient, the elastic band being adjustable as to the selected tightness;
- one or more spaced apart elongated mechanic al fasteners attached to the outside surface of the elastic band, the elongated mechanical fasteners aligned with a longitudinal axis of the elastic band, each elongated mechanical fastener comprises a first surface attachment element having a first side with a multitude of loops and permanently affixed to the outside surface of the elastic band with the multitude of loops facing outward, and a second surface attachment element having a first side with a multitude of hooks facing the first side with the multitude of loops, a second side that is textured to be configured for easy grasping, a first end permanently fastened to the first surface attachment element, a second end, and a length extending longitudinally in removable, mutually engaged contact with the first surface attachment element, the second surface attachment element configured to attach to the first surface attachment element sufficiently to hold a drainage reservoir when filled;
- a handle configured to permit easy removal of the second surface attachment element from the first surfaced attachment element to free the drainage reservoir and subsequent reattachment when the drainage reservoir is emptied and ready for reuse, and the handle comprising an extension of the second surface attachment element from the second end of the second surface attachment element, the extension having its own end and first side with multiple hooks with the first side of the extension folded back upon itself so two surfaces having a multitude of hooks are in contact, the end of the extension is permanently affixed to the second surface attachment element to form the handle which includes an outside textured surface, a length of between 0.25 inches and 0.75 inches and structure that lifts off of and extends outward from the elastic band at an angle of between 10 degrees and 40 degrees from the plane of the elastic band below the handle, for providing a visible and tactile distinction between the handle and the permanently attached first end of the second surface attachment element, as well as providing easier grasping and gripping of the handle, so that the handle is configured to be gripped by a clinician wearing surgical gloves with limited dexterity or gripped by a patient having diminished dexterity or strength; and
- at least one drainage reservoir having an attachment band comprising a loop adapted for receiving one end of said second surface attachment element for engaging the drainage reservoir with the elastic hand for displacing the drainage reservoir within reach of a patient wearing the elastic band;

placing the elastic band around the body part of the patient at the selected tightness to releasably affix the drainage reservoir support to the patient with the drainage reservoirs affixed to drainage lines extending from the patient;

gripping the handle of the one or more elongated mechanical fasteners and easily opening each elongated mechanical fastener, attaching one drainage reservoir to each elongated mechanical fastener, and closing each elongated mechanical fastener to releasably attach the drainage reservoir to the surgical drainage reservoir support and to the patient;

repeating as necessary until all drainage reservoirs are attached to the surgical drainage reservoir support and the patient;

periodically gripping the handle of e or more fasteners and easily open the fastener to remove the drainage reservoir from the surgical drainage reservoir support to empty it; and reattaching the drainage reservoir to the surgical drainage reservoir support to continue collecting fluid.

* * * * *